United States Patent
Funk et al.

(10) Patent No.: US 10,093,593 B2
(45) Date of Patent: Oct. 9, 2018

(54) USE OF CATALYST TO ADJUST PRODUCT DISTRIBUTIONS IN MTO PROCESS

(71) Applicant: UOP LLC, Des Plaines, IL (US)

(72) Inventors: Gregory A. Funk, Carol Stream, IL (US); Andrea G. Bozzano, Northbrook, IL (US); Nicholas J. Schoenfeldt, Chicago, IL (US); Thulasidas Chellppannair, Cave Creek, AZ (US); Wolfgang A. Spieker, Glenview, IL (US); Bipin V. Vora, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/618,016

(22) Filed: Jun. 8, 2017

(65) Prior Publication Data

US 2017/0297973 A1   Oct. 19, 2017

Related U.S. Application Data

(63) Continuation of application No. PCT/US2015/063654, filed on Dec. 3, 2015.

(60) Provisional application No. 62/090,683, filed on Dec. 11, 2014.

(51) Int. Cl.
    *C07C 1/20*    (2006.01)
    *C07C 6/04*    (2006.01)
    *C07C 4/02*    (2006.01)

(52) U.S. Cl.
    CPC .............. *C07C 1/20* (2013.01); *C07C 4/02* (2013.01); *C07C 6/04* (2013.01); *C07C 2529/85* (2013.01); *Y02P 30/42* (2015.11)

(58) Field of Classification Search
    CPC ......... C07C 1/20; C07C 2529/85; C07C 4/02; C07C 6/04
    See application file for complete search history.

(56) References Cited

U.S. PATENT DOCUMENTS

| | | | |
|---|---|---|---|
| 5,914,433 A | 6/1999 | Marker | |
| 6,137,022 A * | 10/2000 | Kuechler | C07C 1/20 585/638 |
| 6,303,839 B1 | 10/2001 | Marker | |
| 6,797,851 B2 * | 9/2004 | Martens | C07C 1/20 585/639 |
| 7,317,133 B2 | 1/2008 | Vora et al. | |
| 7,732,650 B2 * | 6/2010 | Bozzano | C07C 1/20 585/317 |
| 7,763,765 B2 | 7/2010 | Kuechler et al. | |

\* cited by examiner

*Primary Examiner* — Sharon Pregler

(57) ABSTRACT

A process is presented for generating light olefins with the methanol to olefins process from a combination of catalysts. The process controls the product distribution for ethylene, propylene and butylenes, to enable shifting of the product distribution. The process includes passing a second catalyst to a reactor while the process is on-going.

8 Claims, 4 Drawing Sheets

USE OF CATALYST TO ADJUST PRODUCT DISTRIBUTIONS IN MTO PROCESS

CROSS-REFERENCE TO RELATED APPLICATIONS

This application is a Continuation of copending International Application No. PCT/US2015/063654 filed Dec. 3, 2015, which application claims priority from U.S. Provisional Application No. 62/090,683 filed Dec. 11, 2014, the contents of which cited applications are hereby incorporated by reference in their entirety.

FIELD OF THE INVENTION

The present invention relates to the conversion of oxygenates to olefins. In particular, this invention relates to the conversion of methanol to light olefins.

BACKGROUND

The light olefins serve as feed materials for the production of numerous chemicals. Light olefins have traditionally been produced through the processes of steam or catalytic cracking. The limited availability and high cost of petroleum sources, however, has resulted in a significant increase in the cost of producing light olefins from such petroleum sources.

The search for alternative materials for light olefin production has led to the use of oxygenates such as alcohols and, more particularly, to the use of methanol, ethanol, and higher alcohols or their derivatives. The oxygenates are often produced from more plentiful sources of raw materials, such as conversion of natural gas to alcohols, or the production of oxygenates from coal. Molecular sieves such as microporous crystalline zeolite and non-zeolitic catalysts, particularly silicoaluminophosphates (SAPO), are known to promote the conversion of oxygenates to hydrocarbon mixtures, particularly hydrocarbon mixtures composed largely of light olefins.

The amounts of light olefins resulting from such processing can be further increased by reacting, i.e., cracking, heavier hydrocarbon products, particularly heavier olefins such as $C_4$ and $C_5$ olefins, to light olefins. For example, commonly assigned, U.S. Pat. No. 5,914,433 to Marker, the entire disclosure of which is incorporated herein by reference, discloses a process for the production of light olefins comprising olefins having from 2 to 4 carbon atoms per molecule from an oxygenate feedstock. The process comprises passing the oxygenate feedstock to an oxygenate conversion zone containing a metal aluminophosphate catalyst to produce a light olefin stream. A propylene and/or mixed butylene stream is fractionated from said light olefin stream and cracked to enhance the yield of ethylene ($C_2H_4$) and propylene ($C_3H_6$) products. This combination of light olefin product and propylene and butylene cracking in a riser cracking zone or a separate cracking zone provides flexibility to the process which overcomes the equilibrium limitations of the aluminophosphate catalyst. In addition, the invention provides the advantage of extended catalyst life and greater catalyst stability in the oxygenate conversion zone.

With the continued demand for light olefins, there is still a demand for further improvements that will result in increased yields, or reductions in processing costs, or equipment costs.

SUMMARY

While the following is described in conjunction with specific embodiments, it will be understood that this description is intended to illustrate and not limit the scope of the preceding description and the appended claims.

A first embodiment of the invention is a process producing olefins in a methanol to olefins conversion process, comprising passing a catalyst feed combination to an MTO reactor comprising at least two different types of catalyst to the MTO reactor in a fluidized bed reactor system; passing an oxygenate stream to an MTO reactor, for converting oxygenates to olefins, to generate an effluent stream comprising olefins, and having an olefin product distribution; sampling the effluent stream to measure the propylene to ethylene to butylenes product distribution; and adjusting the catalyst feed combination to the MTO reactor. An embodiment of the invention is one, any or all of prior embodiments in this paragraph up through the first embodiment in this paragraph wherein the MTO reactor generates a catalyst effluent stream, further comprising passing the catalyst effluent stream to a catalyst regenerator to generate a regenerated catalyst stream. An embodiment of the invention is one, any or all of prior embodiments in this paragraph up through the first embodiment in this paragraph further comprising passing a portion of the regenerated catalyst stream to a storage system. An embodiment of the invention is one, any or all of prior embodiments in this paragraph up through the first embodiment in this paragraph further comprising passing one type of catalyst from a first catalyst storage unit to the MTO reactor. An embodiment of the invention is one, any or all of prior embodiments in this paragraph up through the first embodiment in this paragraph further comprising passing the effluent stream to a dewatering column to generate a dewatered stream comprising light olefins. An embodiment of the invention is one, any or all of prior embodiments in this paragraph up through the first embodiment in this paragraph further comprising passing the dewatered stream to a compressor to generate a compressed process stream. An embodiment of the invention is one, any or all of prior embodiments in this paragraph up through the first embodiment in this paragraph further comprising passing the compressed process stream to a DME recovery unit to generate a DME effluent stream comprising olefins and a DME recycle stream comprising DME. An embodiment of the invention is one, any or all of prior embodiments in this paragraph up through the first embodiment in this paragraph further comprising passing the effluent stream to a light olefins recovery unit to generate an ethylene product stream, a propylene product stream and a heavies stream. An embodiment of the invention is one, any or all of prior embodiments in this paragraph up through the first embodiment in this paragraph further comprising passing the heavies stream to an olefin cracking unit to generate an olefin cracking process stream comprising light olefins; and passing the olefins process stream to the light olefins recovery unit. An embodiment of the invention is one, any or all of prior embodiments in this paragraph up through the first embodiment in this paragraph further comprising passing a first catalyst feed comprising a first catalyst to a catalyst mixing unit; passing a second catalyst feed comprising a second catalyst to the catalyst mixing unit to generate the catalyst feed combination; and passing the catalyst feed combination to the MTO reactor. An embodiment of the invention is one, any or all of prior embodiments in this paragraph up through the first embodiment in this paragraph further comprising operating the light olefins recovery unit to generate a butene product stream. An embodiment of the invention is one, any or all of prior embodiments in this paragraph up through the first embodiment in this paragraph further comprising passing a portion of the ethylene product stream and a portion of the butene product stream to a metathesis reactor to generate a propylene stream and a by-products stream.

A second embodiment of the invention is a process for the production of light olefins comprising passing a first catalyst feed comprising a first catalyst to an MTO reactor wherein the MTO reactor in a fluidized bed reactor system; passing an oxygenate stream to an MTO reactor to generate an effluent stream comprising olefins, and having a propylene to ethylene product distribution, for converting oxygenates to olefins; sampling the effluent stream to measure the propylene to ethylene to butylenes product distribution; continuing the first catalyst feed to the MTO reactor until a second olefins product distribution is desired; discontinuing passing the first catalyst feed to the MTO reactor; passing a second catalyst feed comprising a second catalyst to the MTO reactor sampling the effluent stream to measure the propylene to ethylene to butylenes product distribution; and continuing the second catalyst feed to the MTO reactor until a new propylene to ethylene to butylenes product distribution is achieved. An embodiment of the invention is one, any or all of prior embodiments in this paragraph up through the second embodiment in this paragraph further comprising passing the effluent stream to a light olefins recovery unit to generate an ethylene stream, a propylene stream, and a heavies stream. An embodiment of the invention is one, any or all of prior embodiments in this paragraph up through the second embodiment in this paragraph further comprising passing the heavies stream to an olefins cracking unit to generate an olefins cracking effluent stream; and passing the olefins cracking effluent stream to the light olefins recovery unit. An embodiment further comprising generating a butenes stream in the light olefins recovery unit. An embodiment of the invention is one, any or all of prior embodiments in this paragraph up through the second embodiment in this paragraph further comprising passing a portion of the ethylene stream and a portion of the butenes stream to a metathesis unit to generate a methathesis stream comprising propylene.

A third embodiment of the invention is a process producing olefins in a methanol to olefins conversion process, comprising splitting an oxygenate feed into two portions; passing a first portion of the oxygenate feed to a first MTO reactor comprising a first catalyst to generate a first MTO reactor effluent; passing a second portion of the oxygenate feed to a second MTO reactor comprising a second catalyst to generate a second MTO reactor effluent; combining the first reactor effluent and the second reactor effluent to generate a combined effluent stream; sampling the combined effluent stream to measure the propylene to ethylene to butylenes product distribution; and adjusting the splitting of the oxygenate feed into two portions to further adjust the combined product stream. An embodiment of the invention is one, any or all of prior embodiments in this paragraph up through the third embodiment in this paragraph further comprising passing the combined effluent stream to a DME recovery unit to generate an olefins process stream and a DME recycle stream. An embodiment of the invention is one, any or all of prior embodiments in this paragraph up through the third embodiment in this paragraph further comprising passing the olefins process stream to a light olefins recovery unit to generate an ethylene stream, a propylene stream, and a heavies stream.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

Other objects, advantages and applications of the present invention will become apparent to those skilled in the art from the following detailed description and drawings.

DETAILED DESCRIPTION

Figure 1:
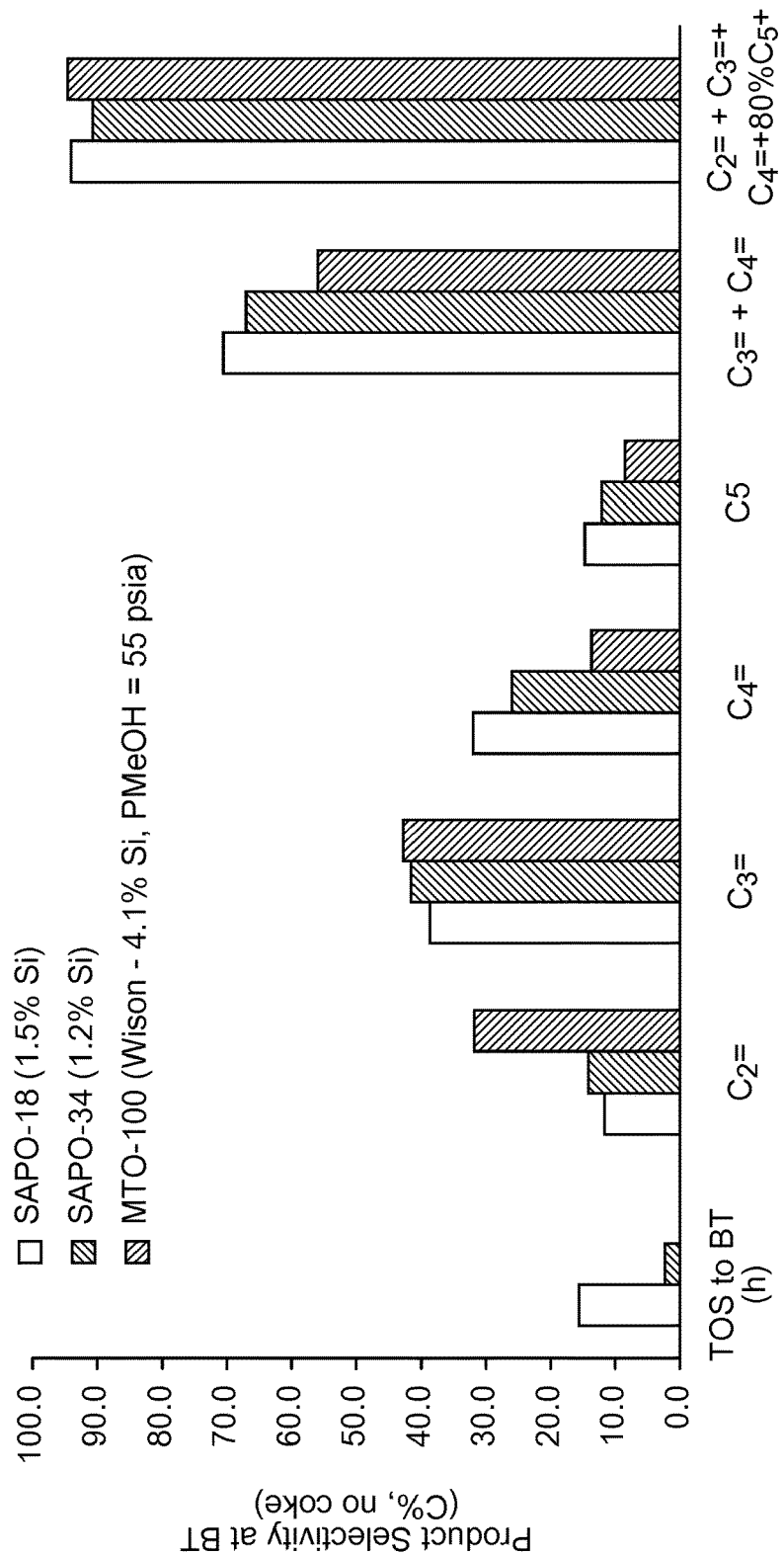
FIG. 1 product distribution for three catalysts.

The production of light olefins, ethylene and propylene, are important precursors for products today, most notably, the principal products are polyethylene and polypropylene. The source of these precursors has been mainly from the cracking of naphtha. Increasingly, other sources for the production of light olefins is sought due to cost considerations and availability of raw materials. Oxygenate, notably methanol, can be converted and is increasingly being used. Methanol can be generated from several sources, including natural gas and coal.

The methanol to olefin (MTO) process has been successfully commercialized. U.S. Pat. No. 6,303,839 presents an integrated MTO-olefin cracking process. The oxygenate feedstock is catalytically converted over a silicoaluminophosphate (SAPO) catalyst. The increase in light olefin production is also described in U.S. Pat. No. 7,317,133 wherein the production of heavier olefins are directed to an olefin cracking reactor to generate a process stream comprising light olefins. The olefin cracking process utilizes a different catalyst from a family of crystalline silicate having an WI or MEL. Examples of these catalysts include ZSM-5 or ZSM-11.

Additional process developments continue to be generated, such as U.S. Pat. No. 7,568,016 that integrates the MTO with an ethylene dimerization process and metathesis process for increasing the propylene yields. The dimerization process can also be used to increase the heavier olefins for other purposes. U.S. Pat. No. 7,732,650 describes a process for the separation of butenes, along with isomerization and metathesis reactions.

Processes are also developed that operate around control conditions of the reactor, such as U.S. Pat. No. 6,137,022, wherein the reaction zone is operated to contain a restricted amount of catalyst, containing 15 volume percent or less, and operation is controlled to limit conversion of the feedstock to between 80 and 99%.

Other aspects include controlling the process with modifications of the catalyst, such as limiting the Si/Al2 ratio to between 0.10 and 0.32 as in U.S. Pat. No. 7,763,765.

While there are many similar patents that cover integrated MTO-OCP process to maximize ethylene and propylene, none of these processes has flexibility to control the Propylene to Ethylene (P/E) product ratio. The P/E product ratio is largely determined by the MTO and OCP reactor yields. A high P/E ratio, preferably more than 3 is desirable due to the increased demand for propylene. Due to this increase in demand for higher propylene over ethylene, it has been discovered that changing the catalyst preference and increasing the pressure substantially has changed not only the product ratios in the MTO process, but the catalyst deactivation rate has been found to decrease, thereby enabling longer cycle times and improved economics.

The changing market for different light olefins leads chemical producers to desire flexibility in changing the product distributions. Typically, the control of the product distributions is dictated by the methanol to olefins (MTO) conversion process, and the particular catalyst for producing a given product distribution. The product distribution can also be modified by some downstream process, such as olefin cracking and metathesis.

The present invention provides for modifying the product distribution through a blending of catalysts, wherein each catalyst generates a different product distribution. FIG. 1 shows a product distribution for three different catalysts: SAPO-18 with 1.5% Si, SAPO-34 with 1.2% Si, and MTO-100 with 4.1% Si.

Figure 2:
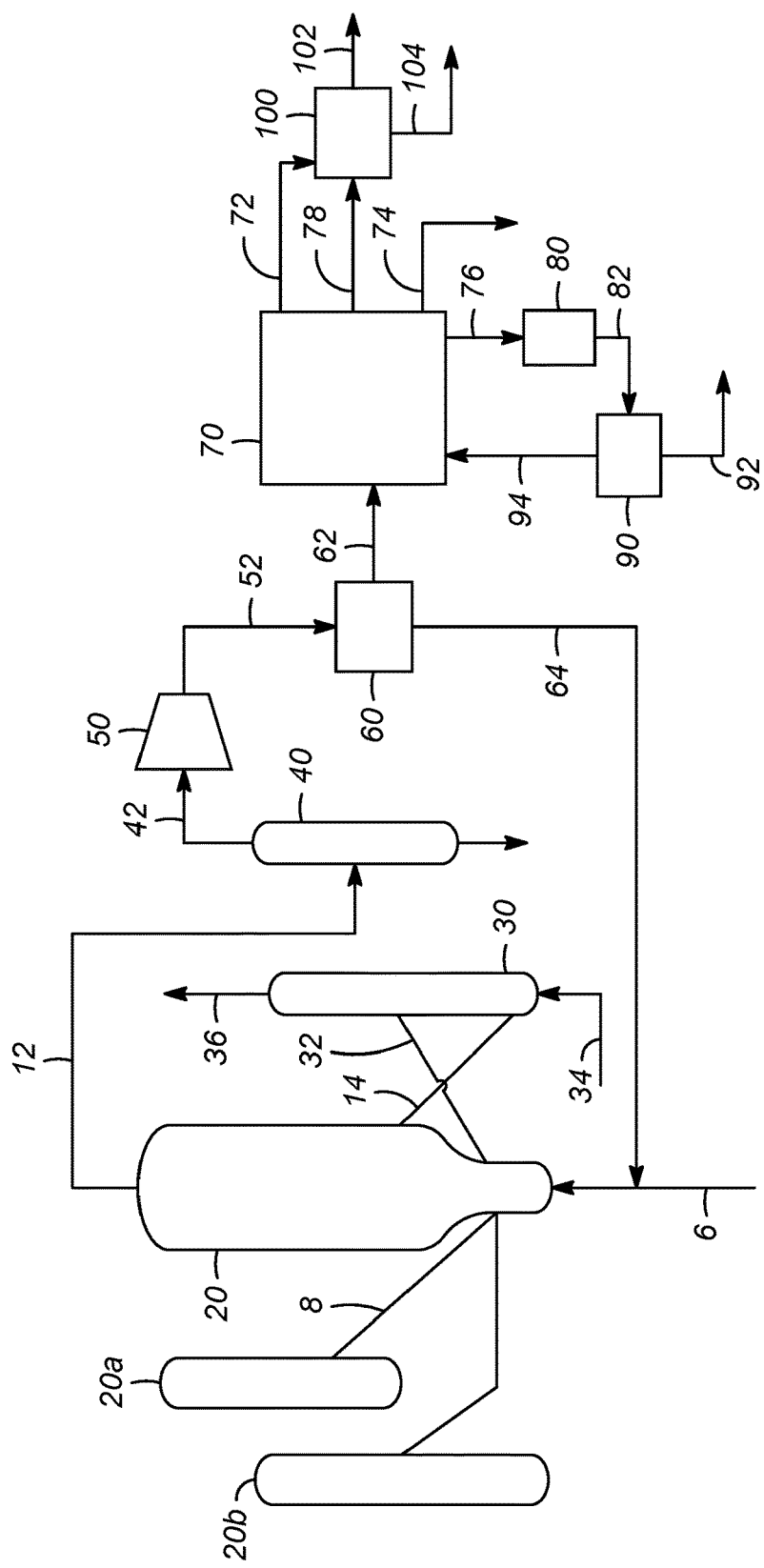
FIG. 2 shows a first embodiment of the process.

A process for producing olefins in a methanol to olefins conversion process is shown in FIG. 2. The process includes passing a catalyst feed combination 8 to an MTO reactor 10. The catalyst feed combination comprises at least two different types of catalysts that are stored in a catalyst storage vessel 20a. The MTO reactor 10 is a fluidized bed reactor system with the catalyst flowing between the reactor 10 and a regenerator 30. An oxygenate stream 6 is passed to the MTO reactor, where it is converted to an effluent stream 12 comprising olefins, and the effluent stream 12 has an olefin product distribution. The effluent stream 12 is sampled to measure the propylene to ethylene ratio. To adjust the propylene to ethylene ratio, the catalyst feed 8 is adjusted to shift the product distribution. A preferred oxygenate feed comprises alcohols and ethers, with a more preferred oxygenate feed comprising methanol.

The process further includes generating a catalyst effluent stream 14, wherein the catalyst effluent stream 14 is passed to a catalyst regenerator 30 to generate a regenerated catalyst stream 32. The process can further comprising passing a portion of the regenerated catalyst stream 32 to a catalyst storage system, wherein the catalyst storage system can comprise one or more catalyst storage vessels 20a, b. The regenerator 30 includes an air source 34 for combusting carbon deposits on the catalyst and generates a regen gas effluent stream 36.

The process can include passing a first type of catalyst from a first catalyst storage unit to the MTO reactor 10, and passing a second type of catalyst from a second catalyst storage unit 20b to the MTO reactor.

The process further includes passing the effluent stream 12 to a dewatering column 40 to generate a dewatered stream 42 comprising light olefins. The dewatered stream 42 is passed to a compressor 50 to generate a compressed process stream 52. The compressed process stream 52 is passed to a dimethyl ether (DME) recovery unit 60 to generate a DME effluent stream 62 comprising olefins and a DME recycle stream 64 comprising dimethyl ether. The DME recycle stream 64 is mixed with the oxygenate feedstream 6 and passed back to the MTO reactor 10.

The DME effluent stream 62 is passed to a light olefins recovery unit 70 to generate an ethylene product stream 72, a propylene product stream 74, and a heavies product stream 76. The process can further include passing the heavies stream 76 to an olefin cracking unit 80 to generate an olefin cracking process stream 82 comprising light olefins. The olefins process stream 2 is separated in a separation section 90 to generate a by-products stream 92 and a light olefins stream 94. The light olefins stream 94 is passed to the light olefins recovery unit 70.

The light olefins recovery unit 70 comprises several distillation columns and other process equipment for separating the light olefins into separate product streams.

The light olefins recovery unit 70 can be operated to generate a butene product stream 78. The process can further include passing a portion of the ethylene product stream 72 and a portion of the butene product stream 78 to a metathesis reactor 100 to generate a propylene stream 102 and a by-products stream 104.

The process can include passing a first catalyst feed comprising a first catalyst to a catalyst mixing unit, passing a second catalyst feed comprising a second catalyst to the catalyst mixing unit to generate the catalyst feed combination, and then passing the catalyst feed combination to the MTO reactor.

In one embodiment, the process includes passing a first catalyst feed comprising a first catalyst to an MTO reactor, wherein the MTO reactor is a fluidized bed reactor system. An oxygenate stream is passed to the MTO reactor, operated at reaction conditions to generate an effluent stream comprising olefins, and having a product distribution containing a propylene to ethylene ratio. The effluent stream is sampled to measure the propylene to ethylene ratio. The first catalyst is continued to be fed to the MTO reactor until a second product distribution is desired. The first catalyst feed to the MTO reactor is discontinued. A second catalyst feed comprising a second catalyst is fed to the MTO reactor to generate a second MTO reactor effluent stream. the second effluent stream is sampled, and the propylene to ethylene ratio is measured. The second catalyst feed is continued until a new propylene to ethylene product distribution is desired.

The process further includes passing the effluent stream to a light olefins recovery unit to generate an ethylene stream, a propylene stream and a heavies stream.

Figure 3:
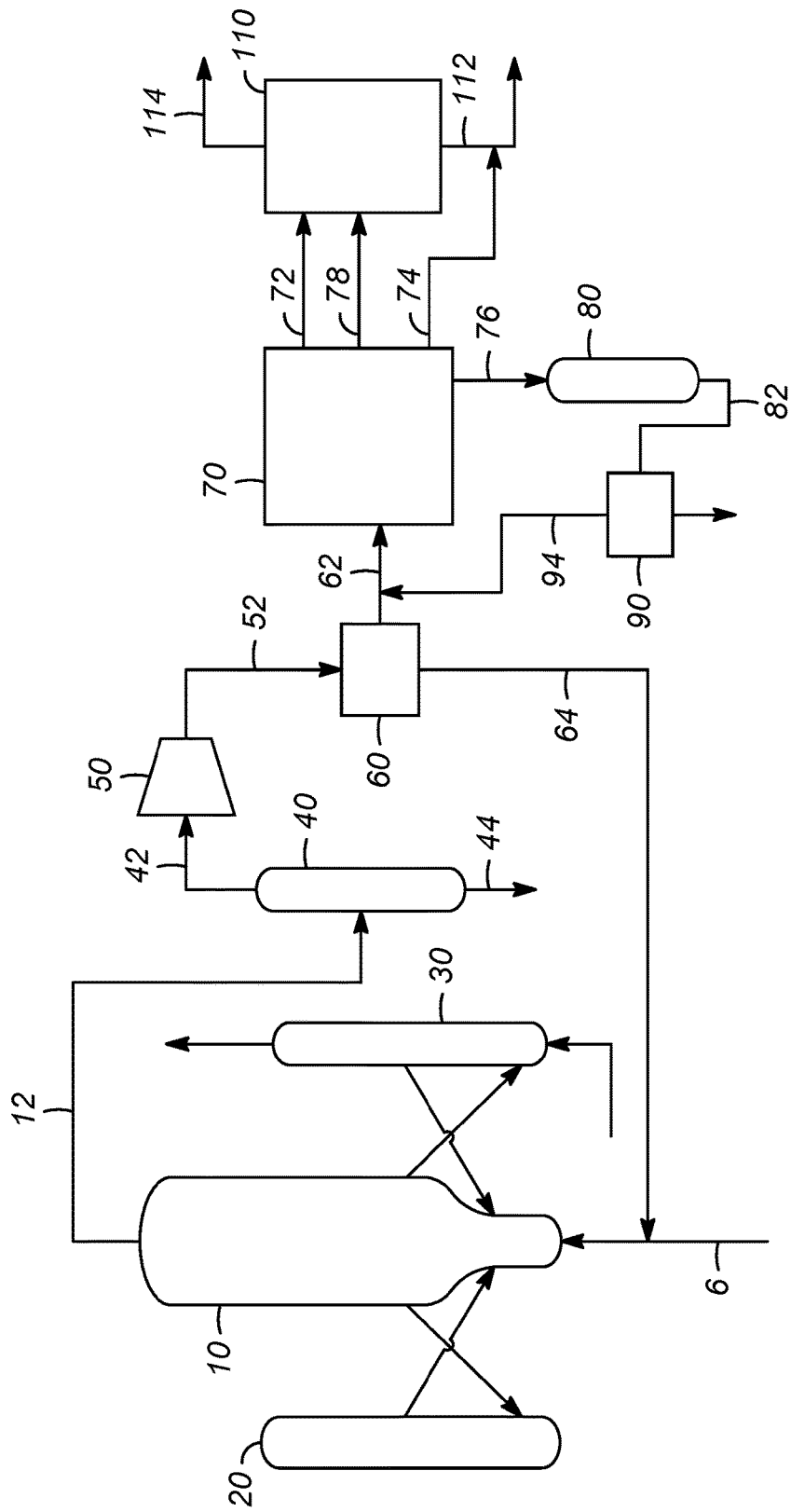
FIG. 3 shows a second embodiment of the process.

In one embodiment, the process, as shown in FIG. 3, is operated to generate a high heavies content, wherein the heavies comprises C4+ olefins, relative to the ethylene content. The process includes passing an oxygenate feedstream 6 to the MTO reactor 10 to generate an effluent stream 12 comprising olefins, but with a relatively high heavy olefin content. The effluent stream 12 is passed to the dewatering column 40 to generate a dewatered stream 42. The dewatered stream 42 is compressed to generate a compressed stream 52. The compressed stream 52 is processed to remove DME in a DME recovery unit 60. to generate an olefins effluent stream 62.

The light olefins recovery unit 70 separates the olefins effluent stream 62 into an ethylene stream 72, a propylene stream 74, a heavies stream 76 comprising C5+ hydrocarbons, and an n-butenes stream 78. The ethylene stream 72 and the n-butenes stream 78 are passed to a metathesis unit 110 to generate a propylene stream 112 and a by-products stream 114.

Figure 4:
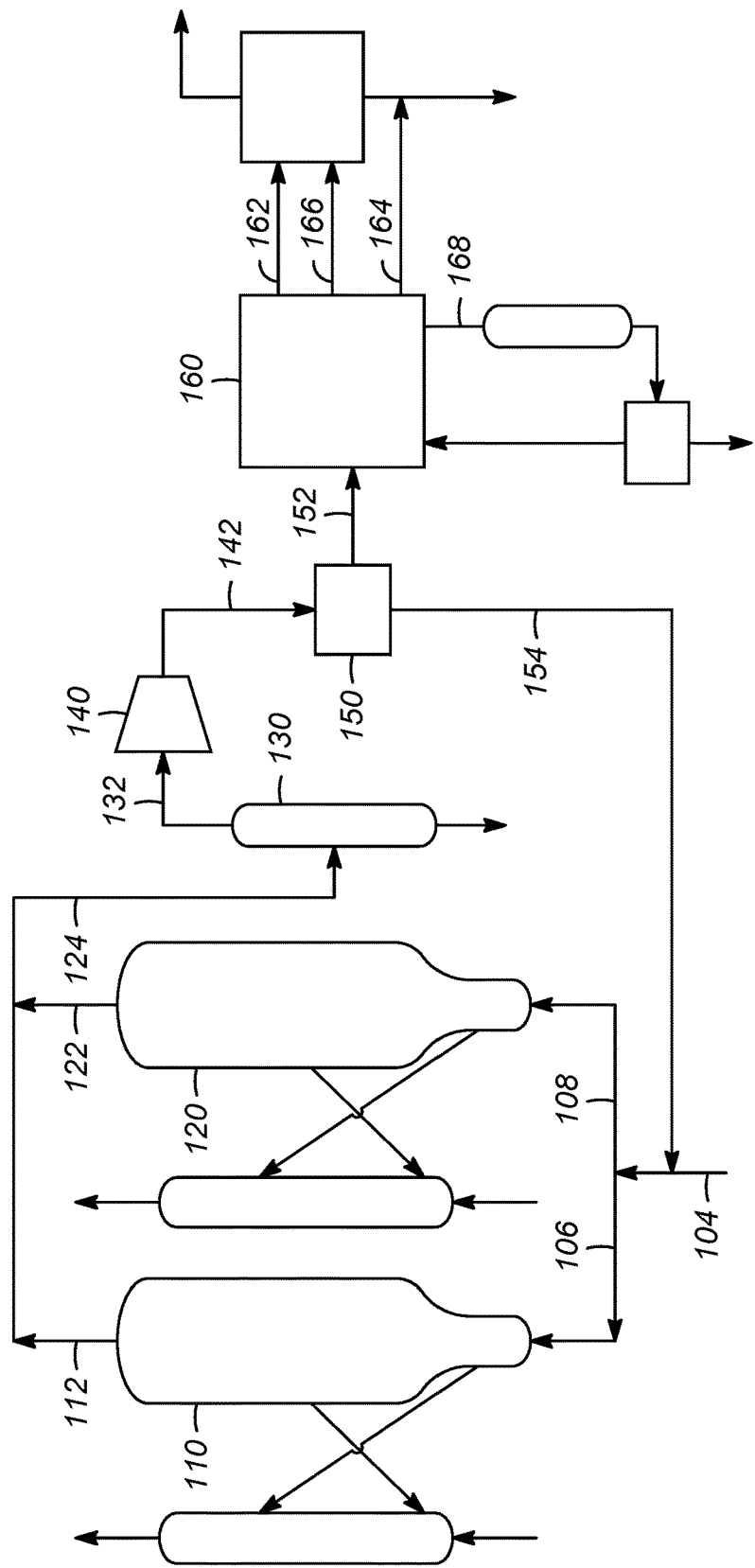
FIG. 4 shows a third embodiment.

In a third embodiment, the process for producing olefins from oxygenates comprises utilizing fixed beds for the MTO reactors, as shown in FIG. 4. The process includes splitting an oxygenate feed 104 into two portions 106 and 108. A first portion 106 is passed to a first MTO reactor 110 having a first catalyst to generate a first MTO reactor effluent stream 112. A second portion 108 is passed to a second MTO reactor 120 having a second catalyst to generate a second MTO reactor effluent stream 122. The first effluent stream 112 and the second effluent stream 122 are combined to form a combined stream 124. The combined stream 124 can be sampled to measure the propylene to ethylene product ratio. This provides feedback to adjust the split of the oxygenate feedstream 106 into two portions.

The combined stream 124 is passed to a dewatering column 130 to generate a dewatered process stream 132. The dewatered process stream 132 is passed to a compressor 140 to generate a compressed process stream 142. The compressed process stream 142 is passed to a DME recovery unit 150 to generate a DME olefins stream 152 and a DME recycle stream 154. The DME recycle stream 154 is passed back to the feed to the MTO reactors. The DME olefins stream 152 is passed to a light olefins recovery unit 160 to generate an ethylene stream 162, a propylene stream 164, a butene stream 166 and a heavies stream 168.

While the two fluidized fixed bed MTO reactor system is shown for utilizing two catalysts in two separate reactors, this can also be operated as two fluidized bed reactor systems with each reactor system utilizing a different catalyst. The two reactor system can also allow for different operating conditions for the different catalysts. This provides flexibility to optimize each reactor separately. A pressure control valve can be utilized when combining the two effluent streams from the two reactors.

Recent testing has demonstrated that different MTO catalysts give very different yield patterns. This can be seen in FIG. 1 for three different MTO catalysts. In a similar manner, changing the % Si in an MTO catalyst can also shift the yield pattern.

Since the typical MTO process is based on a fluidized bed system, as a catalyst is removed from a reactor, the reactor can be emptied of that catalyst, and a second catalyst can be transported from a separate catalyst storage vessel to replace the removed catalyst. This provides for maintaining the catalysts as separate components.

Table 1 shows the results based on laboratory yield data for the conventional SAPO-34 catalyst and for a second catalyst, or SAPO-18 catalyst. The oxygenate used was methanol. Both are tested under conditions of a temperature of 400° C. and a methanol partial pressure of 1.34 MPa. Columns 2 and 3 summarize the yields for SAPO-34 without OCP and with OCP. The OCP is estimated from simulations based on known operations. For the SAPO-34 the propylene to ethylene (P/E) yields increased from 1.39 to 1.68.

Similarly, columns 4 and 5 summarize the yields for SAPO-18 without and with OCP. The SAPO-18 results gave a P/E ratio of 3.25 and 3.55. As demand changes for propylene, or ethylene, the catalyst can be changed, or combined to shift the yields according to demand.

TABLE 1

| Catalyst 1 | SAPO-34 | SAPO-34 | SAPO-18 | SAPO-18 |
|---|---|---|---|---|
| Catalyst 1 Amount, % | 100.00% | 100.00% | 100.00% | 100.00% |
| Catalyst 2 | — | — | — | — |
| Catalyst 2 Amount, % | 0.00% | 0.00% | 0.00% | 0.00% |
| OCP | No | Yes | No | No |
| Metathesis | No | No | No | No |
| C2= | 31.0% | 34.9% | 12.0% | 19.8% |
| C3= | 43.0% | 58.6% | 39.0% | 70.3% |
| C4= | 14.0% | 0.0% | 32.0% | 0.0% |
| C5+= | 9.0% | 0.0% | 14.0% | 0.0% |
| MTO Other Byproducts | 3.0% | 3.0% | 3.0% | 3.0% |
| OCP Byproducts | 0.0% | 3.5% | 0.0% | 6.9% |
| Metathesis Byproducts | 0.0% | 0.0% | 0.0% | 0.0% |
| C3=/C2= | 1.39 | 1.68 | 3.25 | 3.55 |
| Total | 100.0% | 100.0% | 100.0% | 100.0% |

The process, when including metathesis increases the propylene yields while sacrificing some ethylene. This may be desirable as ethylene is of lower value than the propylene. The metathesis process also utilizes some of the heavier components, in particular butenes, which also have a lower value than propylene.

Table 2 shows the results of combining two catalysts in the process of producing propylene. The table shows the yields of two catalysts separately, and of a combination of the two catalysts. The relative amounts of product can therefore be determined by adjusting the relative amounts of the two different catalysts.

The process shows that adding some SAPO-34 to a SAPO-18 system increases the propylene over either catalyst alone, when the process includes metathesis. This is due to SAPO-18 having a lower yield of ethylene and therefore not converting as much of the heavier olefins to propylene. The addition of a relatively small amount of SAPO-34 increases the yield of ethylene, which in turn is passed to the metathesis reactor, and resulting in an increase in the overall propylene yields.

TABLE 2

| Catalyst 1 | SAPO-34 | SAPO-18 | SAPO-18 |
|---|---|---|---|
| Catalyst 1 Amount, % | 100.00% | 100.00% | 94.05% |
| Catalyst 2 | — | — | SAPO-34 |
| Catalyst 2 Amount, % | 0.00% | 0.00% | 5.95% |
| OCP | Yes | Yes | Yes |
| Metathesis | Yes | Yes | Yes |
| C2= | 25.5% | 0.0% | 0.0% |
| C3= | 69.2% | 90.7% | 94.0% |
| C4= | 0.0% | 3.2% | 0.0% |
| C5+= | 0.0% | 0.0% | 0.0% |
| MTO Other Byproducts | 3.0% | 3.0% | 3.0% |
| OCP Byproducts | 1.4% | 2.1% | 2.1% |
| Metathesis Byproducts | 0.9% | 0.9% | 1.0% |
| C3=/C2= | 2.71 | #DIV/0! | #DIV/0! |
| Total | 100.0% | 100.0% | 100.0% |

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for the production of light olefins comprising:
    passing a first catalyst feed comprising a first catalyst to an MTO reactor wherein the MTO reactor in a fluidized bed reactor system;
    passing an oxygenate stream to an MTO reactor to generate an effluent stream comprising olefins, and having a propylene to ethylene product distribution, for converting oxygenates to olefins;
    sampling the effluent stream to measure the propylene to ethylene to butylenes product distribution;
    continuing the first catalyst feed to the MTO reactor until a second olefins product distribution is desired;
    discontinuing passing the first catalyst feed to the MTO reactor;
    passing a second catalyst feed comprising a second catalyst to the MTO reactor;
    sampling the effluent stream to measure the propylene to ethylene to butylenes product distribution; and
    continuing the second catalyst feed to the MTO reactor until a new propylene to ethylene to butylenes product distribution is achieved.

2. The process of claim 1 further comprising passing the effluent stream to a light olefins recovery unit to generate an ethylene stream, a propylene stream, and a heavies stream.

3. The process of claim 2 further comprising:
passing the heavies stream to an olefins cracking unit to generate an olefins cracking effluent stream; and
passing the olefins cracking effluent stream to the light olefins recovery unit.

4. The process of claim 2 further comprising generating a butenes stream in the light olefins recovery unit.

5. The process of claim 4 further comprising passing a portion of the ethylene stream and a portion of the butenes stream to a metathesis unit to generate a methathesis stream comprising propylene.

6. A process producing olefins in a methanol to olefins conversion process, comprising:
splitting an oxygenate feed into two portions;
passing a first portion of the oxygenate feed to a first MTO reactor comprising a first catalyst to generate a first MTO reactor effluent;
passing a second portion of the oxygenate feed to a second MTO reactor comprising a second catalyst to generate a second MTO reactor effluent;
combining the first reactor effluent and the second reactor effluent to generate a combined effluent stream;
sampling the combined effluent stream to measure the propylene to ethylene to butylenes product distribution; and
adjusting the splitting of the oxygenate feed into two portions to further adjust the combined product stream.

7. The process of claim 6 further comprising passing the combined effluent stream to a DME recovery unit to generate an olefins process stream and a DME recycle stream.

8. The process of claim 7 further comprising passing the olefins process stream to a light olefins recovery unit to generate an ethylene stream, a propylene stream, and a heavies stream.

* * * * *